US012709230B2

(12) United States Patent
Lee et al.

(10) Patent No.: US 12,709,230 B2
(45) Date of Patent: Aug. 18, 2026

(54) BIDIRECTIONAL STERILIZATION TYPE CONSOLE ARM REST DEVICE AND VEHICLE INCLUDING SAME

(71) Applicants: HYUNDAI MOTOR COMPANY, Seoul (KR); KIA CORPORATION, Seoul (KR); KOLON GLOTECH, INC., Seoul (KR); DUCK YANG INDUSTRY CO., LTD., Ulsan (KR)

(72) Inventors: Jae-Seung Lee, Hwaseong-si (KR); Byoung-Chul Park, Seosan-si (KR); Jae-Yong Lee, Suwon-si (KR)

(73) Assignees: HYUNDAI MOTOR COMPANY, Seoul (KR); KIA CORPORATION, Seoul (KR); KOLON GLOTECH, INC., Seoul (KR); DUCK YANG INDUSTRY CO., LTD., Ulsan (KR)

( * ) Notice: Subject to any disclaimer, the term of this patent is extended or adjusted under 35 U.S.C. 154(b) by 457 days.

(21) Appl. No.: 18/514,923

(22) Filed: Nov. 20, 2023

(65) Prior Publication Data

US 2025/0018869 A1 Jan. 16, 2025

(30) Foreign Application Priority Data

Jul. 14, 2023 (KR) ........................ 10-2023-0091981

(51) Int. Cl.

| | |
|---|---|
| ***B60R 7/04*** | (2006.01) |
| ***A61L 2/084*** | (2026.01) |
| ***A61L 2/088*** | (2026.01) |
| ***B60N 2/75*** | (2018.01) |

(52) U.S. Cl.
CPC ................ *B60R 7/04* (2013.01); *A61L 2/084* (2013.01); *A61L 2/088* (2013.01); *B60N 2/793* (2018.02)

(58) Field of Classification Search
CPC ... B60R 7/04; B60R 2011/0007; A61L 2/084; A61L 2/088; A61L 2202/11; A61L 2/10; A61L 2/08; A61L 2/26; B60N 2/793; B60N 2/75; B60N 2/79; F21K 9/61; F21V 7/00; F21V 23/005; F21V 33/00; F21V 2200/20; G02B 6/0001; F21Y 2115/10
USPC .................................................... 250/455.11
See application file for complete search history.

(56) References Cited

FOREIGN PATENT DOCUMENTS

KR 1020220170314 * 12/2022

* cited by examiner

*Primary Examiner* — Michael Maskell
(74) *Attorney, Agent, or Firm* — Fish & Richardson P.C.

(57) ABSTRACT

A bidirectional sterilization type console arm rest device includes a first sterilization light generator configured to generate visible light emitted to front surfaces of belongings in an arm rest, and a second sterilization light generator configured to generate visible light emitted to rear surfaces of belongings in a console inner space. Therefore, sterilization by the visible light can solve the problem of harmfulness to the human body and the problem of light directivity and transmittance and maximize a sterilization effect by light diffusion of a light guiding film and, particularly, due to a separation structure of a light source and a light guiding film, the light guiding film also comes out of a belongings storage space so that usability of the tray as well as utilization of the storage space can be increased.

22 Claims, 9 Drawing Sheets

<CROSS SECTION A-A>

<TRANSMITTANCE PERFORMANCE FOR EACH WAVELENGTH>

<STERILIZE BOTH SURFACES OF BELONGINGS>

BIDIRECTIONAL STERILIZATION TYPE CONSOLE ARM REST DEVICE AND VEHICLE INCLUDING SAME

CROSS-REFERENCE(S) TO RELATED APPLICATIONS

This application claims priority to Korean Patent Application No. 10-2023-0091981, filed on Jul. 14, 2023, which is incorporated herein by reference in its entirety.

TECHNICAL FIELD

The present disclosure relates to a sterilization type console arm rest device, and more particularly, to a bidirectional sterilization type console arm rest device, which simultaneously emits visible light with a 405 nm wavelength in upward and downward directions of a sterilization object, and a vehicle including the same.

BACKGROUND

Generally, a console box installed in a vehicle includes a console storage for accommodating items and an arm rest movably coupled to be opened or closed.

In recent developments, the console box has evolved into a sterilization capable console arm rest device, offering features such as a smartphone stand and a smartphone charging capabilities in addition to its standard storage functions. This enhancement includes the incorporation of a sterilization module for sanitizing smartphones and other items.

As an example, the sterilization type console arm rest device is integrated into an arm rest covering the console's storage area. The sterilization type console includes an ultraviolet C (UVC) light-emitting diode (LED) unit equipped for sterilization, an arm rest tray for placing items requiring sterilization (e.g., a smartphone, a mask, and the like), and an aluminum reflector.

In this design, the UVC light emitted by the LED targets the items placed on the arm rest tray, and the reflector enhances the concentration and effectiveness of the UVC light for greater sterilizing power.

However, since the UVC light in the sterilization type console arm rest device falls within a wavelength range of 100 nm to 280 nm for sterilization, there are concerns about potential harm to humans, directional limitations based on the LED's placement, and limited light transmittance, resulting in reduced UVC wavelength transmission and diffusion.

In addition, in the sterilization type console arm rest device, the UVC LED unit is mounted on an arm rest cover and emits the UVC light from top to bottom, making it challenge to simultaneously sterilize both the front and rear surfaces of items place on the arm rest tray (e.g., a smartphone, a mask, and the like).

SUMMARY

The present disclosure is directed to a bidirectional sterilization type console arm rest device including a first sterilization light generator provided at an arm rest movably coupled to a console storage forming a console inner space in which an arm rest tray where belongings are placed is accommodated, and a second sterilization light generator configured to generate visible light emitted upward to rear surfaces of the belongings in the console inner space, wherein the visible light is generated from a light-emitting diode (LED) mounted on a printed circuit board (PCB) substrate, and the downward emission and the upward emission are performed in a light guiding plate forming a traveling path of the visible light.

In some implementations, the LED and the light guiding plate may be separated and may face each other.

In some examples, the visible light may have a 405 nm wavelength.

In some implementations, the light guiding plate may be made of a light guiding film configured to diffuse the visible light, may diffuse the visible light through a light emitting surface coated with optical ink, and may be provided with any one among a reflector, a photocatalyst reflector, and a photocatalytic extended reflector, which reflect the visible light and are provided on a surface opposite to the light emitting surface.

In some examples, the photocatalyst reflector may be attached to the surface opposite to the light emitting surface by an optical adhesive, may be made of a fabric configured to induce diffused reflection of the visible light and a photocatalyst configured to increase reflectance, and may form a length section of the light guiding plate in which the light diffused reflection induction and the reflectance increase are performed to the same length as the light guiding plate.

In some implementations, the photocatalytic extended reflector may be attached to the surface opposite to the light emitting surface by an optical adhesive, may be made of a fabric configured to induce diffused reflection of the visible light and a photocatalyst configured to increase reflectance, and may be provided with a reflector side wall which extends from the length section of light guiding plate and has the same length as the light guiding plate and which is located at one end portion of the light guide, the light diffused reflection may be included and the reflectance may be increased in the length section of the light guiding plate, and the reflector side wall may generate a sterilizing material through a chemical reaction between some of the visible light emitted from the light emitting surface and a photocatalyst.

In some examples, a power supply unit may be provided in the console storage, and the power supply unit may supply power of a battery to the PCB substrate and the LED and supply the power of the battery through a switch provided at the arm rest.

In some implementations, the power supply unit may include a first power supply connected to the first sterilization light generator, a second power supply connected to the second sterilization light generator, a power connector configured to connect power cables to the first power supply and the second power supply, and a protective cover coupled to the console storage to cover the power connector.

In some examples, the console storage may be provided with a tolerance absorber in a bent portion of a storage inner wall, and the tolerance absorber may absorb a distribution of a mounting position of the arm rest tray with respect to the storage inner wall in the console inner space.

In some implementations, the tolerance absorber may include a guider coupled to an inner wall surface of the console storage and configured to a downward movement of the PCB substrate, a spring coupled to the bent portion of the storage inner wall and configured to support a lower portion of the PCB substrate, and a light guiding plate support panel configured to move the PCB substrate downward by receiving a force applied downward by the light guiding plate when the arm rest tray is located in the bent portion of the storage inner wall.

In some examples, the guider may have a "T" cross section structure, the spring may be compressed and deformed by the downward movement of the PCB substrate, and the light guiding plate support panel may protrude horizontally from a side surface of the PCB substrate.

In some implementations, an arm rest cover may be provided at a lower portion of the arm rest, and the first sterilization light generator may be installed at the arm rest cover.

In some examples, a tray opening may be formed in the arm rest tray, and the tray opening may form a rim on which the belongings are seated.

The present disclosure is also directed to a vehicle including a console arm rest including an arm rest, which is opened in a hinge structure in a console storage where a console inner space is formed, and an arm rest tray, on which belongings are seated and which is detached/attached to the console inner space, and a sterilization module including a first sterilization light generator provided at the arm rest and configured to generate visible light which is emitted downward to front surfaces of the belongings, and a second sterilization light generator provided in the console inner space and configured to generate visible light which is emitted upward to rear surfaces of the belongings.

In some implementations, the armrest can be configured to open within the console storage, creating access to the inner space of the console. For example, the armrest can be movably coupled to the console storage.

In some implementations, the sterilization module may include a power supply unit provided in the console storage, and a tolerance absorber coupled to a storage inner wall bent toward the console inner space of the console storage, the power supply unit may supply power of a battery to the first sterilization light generator and the second sterilization light generator through a switch provided at the arm rest, and the tolerance absorber may absorb a distribution of a mounting position of the arm rest tray with respect to the storage inner wall in the console inner space.

DETAILED DESCRIPTION

Figure 1:
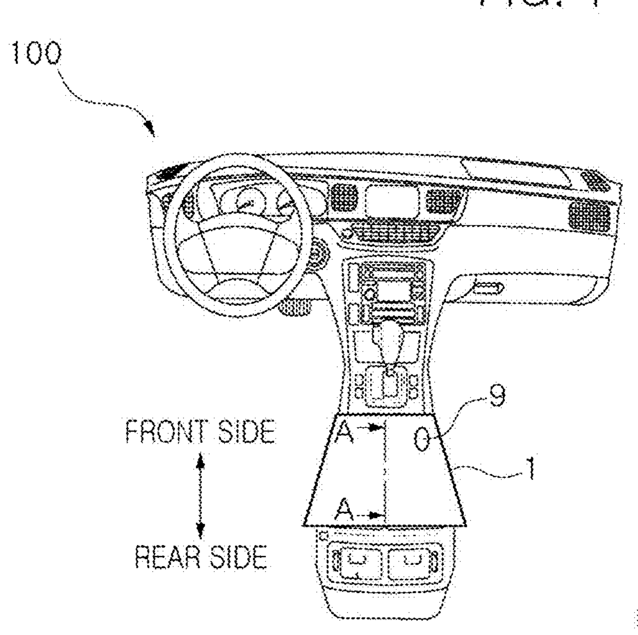
FIG. 1 is a configurational diagram illustrating an example of a bidirectional sterilization type console arm rest device applied to a vehicle.
Figure 1:
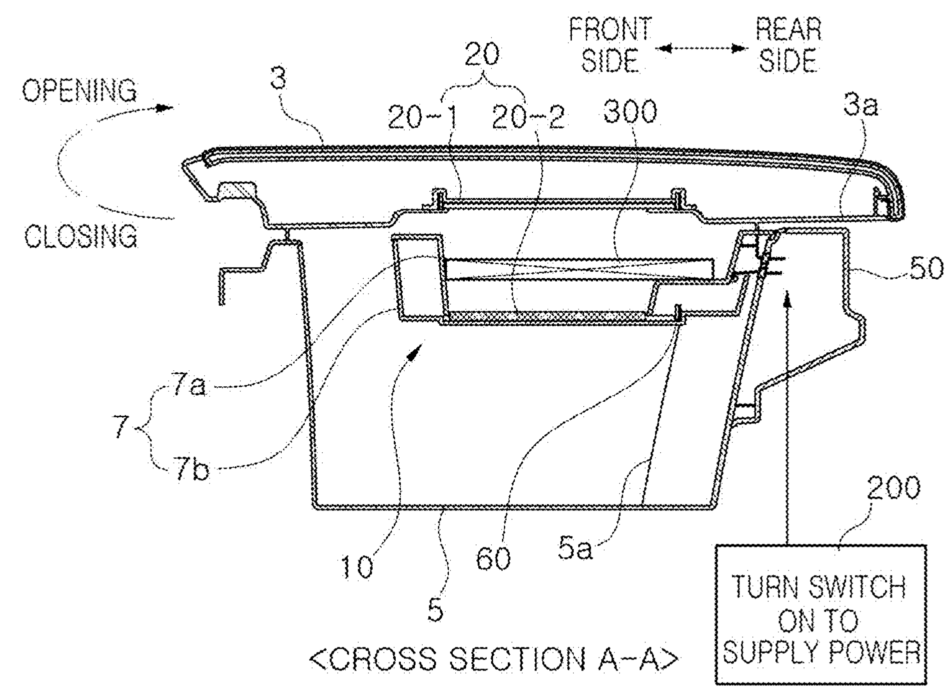

Referring to FIG. 1, a console arm rest device 1 includes console arm rests assembly 3, 5, 7, and 9 and a sterilization module 10, which are installed in a vehicle 100.

Specifically, the console arm rests assembly 3, 5, 7, and 9 are located behind a center fascia where a gear shift lever and the like are installed on a side of a driver's seat of a vehicle and includes an arm rest 3, a console storage 5, an arm rest tray 7, and a switch 9.

For example, the arm rest 3 is provided with a first sterilization light generator 20-1 of the sterilization module 10 and is coupled to an upper portion of the console storage 5 so as to be opened in a hinge opening and closing structure, the console storage 5 is an inner console space for accommodating driver's belongings and the like and the arm rest tray 7 is coupled thereto, and the arm rest tray 7 partitions the inner console space of the console storage 5 and is provided with a second sterilization light generator 20-2 of a sterilization module 10.

In some implementations, the armrest 7 can be configured to open within the console storage, creating access to the inner space of the console. For example, the armrest 7 can be movably coupled to the console storage.

In particular, the arm rest tray 7 includes an upper arm rest tray 7a and a lower arm rest tray 7b, the upper arm rest tray 7a has a box shape and forms an inner tray space in which belongings 300 are accommodated, and the lower arm rest tray 7b is coupled to a lower portion of the upper arm rest tray 7a.

In addition, the upper arm rest tray 7a forms a tray opening 8 (see FIG. 5) in an intermediate portion of the upper arm rest tray 7a to allow the belongings 300 to be seated on a rim of the upper arm rest tray 7a. In this case, the tray opening 8 is drilled in a square or rectangular shape on a bottom surface of the upper arm rest tray 7a, but may be drilled in various shapes, as necessary.

As one example, the switch 9 is provided on the arm rest 3 and is connected to a power supply unit 50 so as to supply, when pressed, power of a battery 200 to a visible light-LED unit 30 (see FIG. 2) of the first and second sterilization light generators 20-1 and 20-2.

Specifically, the sterilization module 10 includes the sterilization light generator 20, the power supply unit 50, and a tolerance absorber 60.

For example, the sterilization light generator 20 includes a first sterilization light generator 20-1 and a second sterilization light generator 20-2, the first sterilization light generator 20-1 is installed in an arm rest cover 3a of the arm rest 3, the second sterilization light generator 20-2 is located at a bottom of the arm rest tray 7 (i.e., the upper arm rest tray 7a).

Therefore, the console arm rest device 1 is characterized as a bidirectional sterilization type console arm rest device 1 which generates downward visible light of the first sterilization light generator 20-1 and upward visible light of the second sterilization light generator 20-2, and thus germs on front and rear surfaces of the belongings 300 are simultaneously sterilized with the upward and downward visible light so that enhancement of a health care function is implemented.

As one example, the power supply unit 50 forms an electrical circuit with battery power of the vehicle 100 and turns the switch 9 on to supply power of the battery 200 to each of the first and second sterilization light generators 20-1 and 20-2.

To this end, the power supply unit 50 is provided in the console storage 5 to form an electrical contact with the arm rest tray 7 (i.e., the upper arm rest tray 7*a*).

Figure 5:
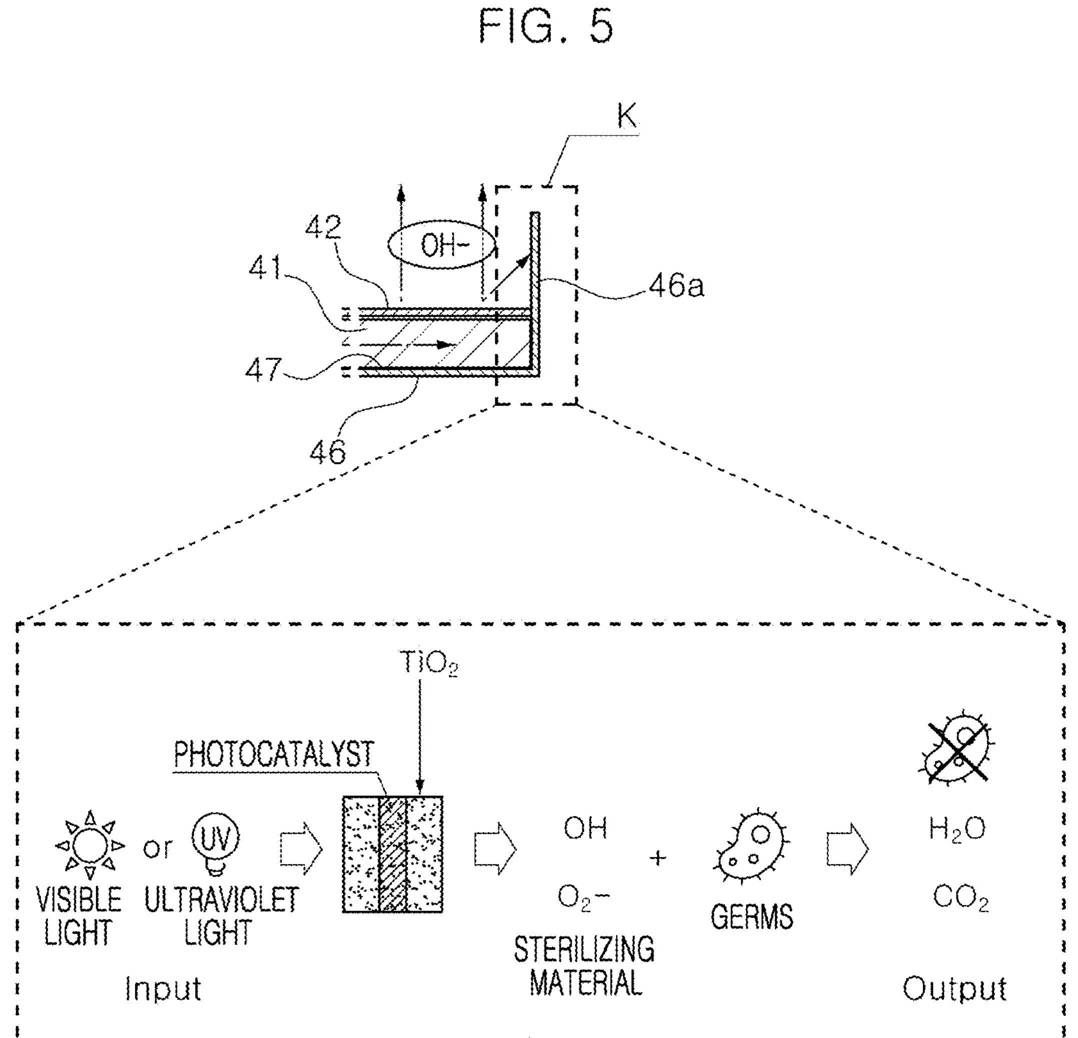
FIG. 5 is a diagram illustrating an example of a state in which an expansion of a reflective area and an increase of sterilization efficiency are implemented by the photocatalytic extended reflector.

As one example, the tolerance absorber 60 is formed using a storage inner wall 5*a* of the console storage 5, and when the arm rest tray 7 (i.e., the upper arm rest tray 7*a*) is coupled to the console storage 5, the tolerance absorber 60 absorbs a distribution of a mounting position of the second sterilization light generator 20-2 with respect to a light guiding plate 41 (see FIG. 5).

Figure 2:
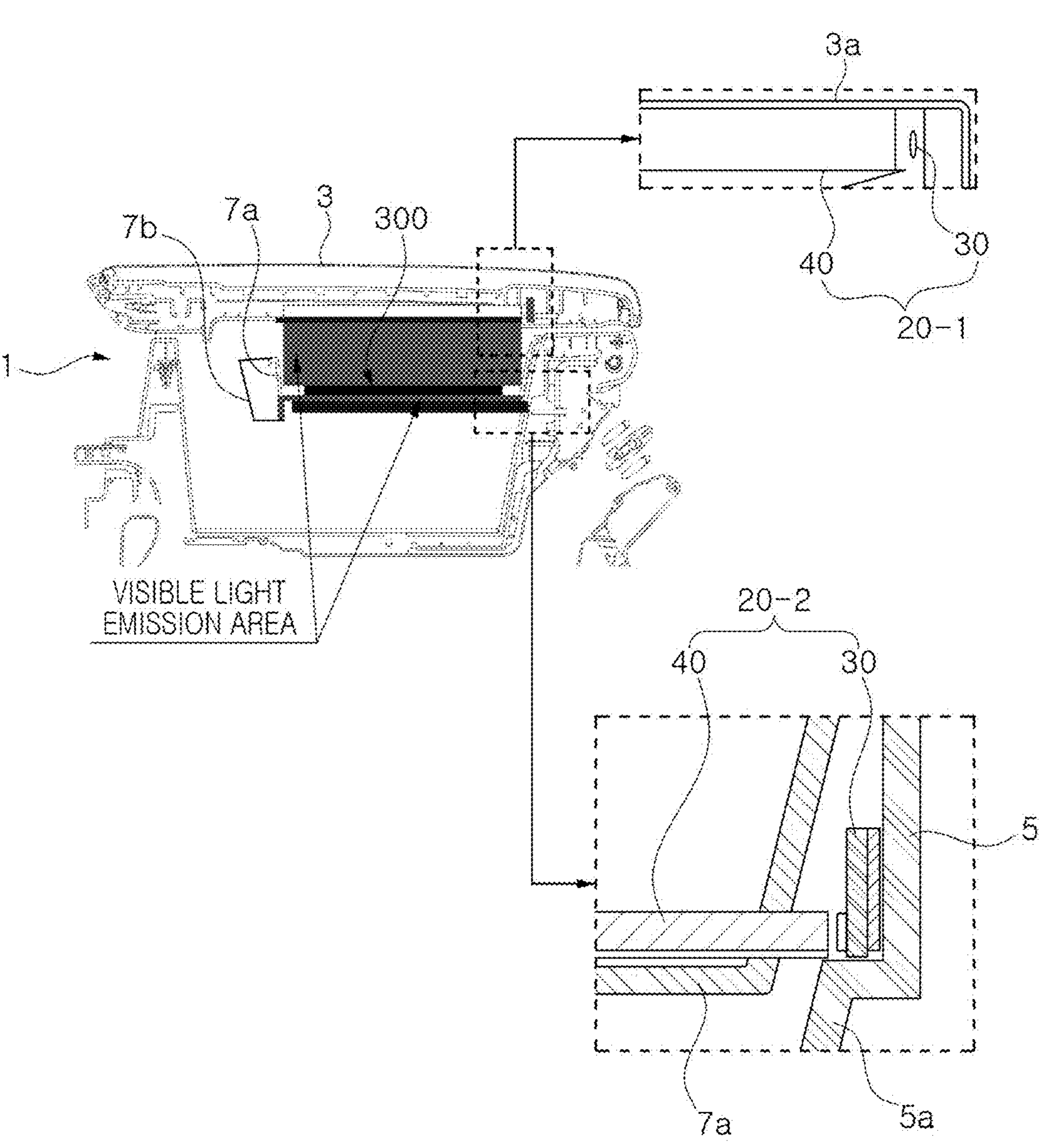
FIG. 2 is a configurational diagram illustrating an example of a sterilization module installed the console arm rest device.
Figure 3:
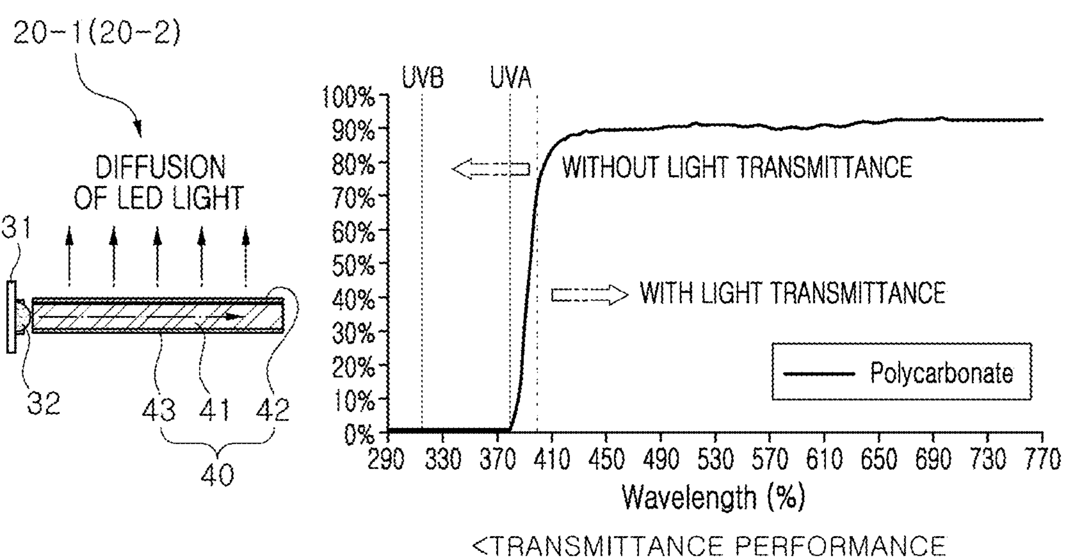
FIG. 3 is a diagram illustrating an example of a light guiding film effect applied to a visible light-light-emitting diode (LED) unit.

Meanwhile, FIGS. 2 and 3 show detailed configurations of the first sterilization light generator 20-1 and the second sterilization light generator 20-2, which constitute the sterilization light generator 20.

Referring to FIG. 2, when the belongings 300 are located on the upper arm rest tray 7*a*, the first sterilization light generator 20-1 generates visible light emitted downward to the front surfaces of the belongings 300 and, simultaneously, the second sterilization light generator 20-2 generates visible light emitted upward to the rear surfaces of the belongings 300. In this case, it is preferable to use the visible light with a 405 nm wavelength.

Therefore, the console arm rest device 1 is characterized as a bidirectional sterilization type console arm rest device 1 which generates downward visible light of the first sterilization light generator 20-1 and upward visible light of the second sterilization light generator 20-2, and thus germs on front and rear surfaces of the belongings 300 are simultaneously sterilized with the upward and downward visible light so that enhancement of a health care function is implemented.

To this end, each of the first and second sterilization light generators 20-1 and 20-2 includes the visible light-LED unit 30 and a light diffusion unit 40 as the same components.

In particular, a separation structure is applied to an LED 32 of the visible light-LED unit 30 and the light guiding plate 41 of the light diffusion unit 40, and due to the separation structure of the LED 32 and the light guiding plate 41, when the arm rest tray 7 is removed from the console storage 5, in a state in which the LED 32 of the second sterilization light generator 20-2 is located in the console storage 5 (i.e., the storage inner wall 5*a*), the light guiding plate 41, together with the arm rest tray 7, comes out of internal space of the console storage 5, it is possible to omit an electrical contact portion of the arm rest tray 7 and increase the tray usage.

Hereinafter, when the visible light-LED unit 30 and the light diffusion unit 40 are applied to the first sterilization light generator 20-1, a description is made as a first printed circuit board (PCB) substrate 31, a first LED 32, and a first light guiding plate 41, and the visible light-LED unit 30 and the light diffusion unit 40 are applied to the second sterilization light generator 20-2, a description is made as a second PCB substrate 31, a second LED 32, and a second light guiding plate 41, but the description will be made as the PCB substrate 31, the LED 32, and the light guiding plate 41 without distinction therebetween.

Referring to FIG. 3, the visible light-LED unit 30 includes the PCB substrate 31 on which various electrical components including semiconductors are integrated, and the LED 32, and the light diffusion unit 40 includes the light guide. plate 41, an optical ink 42, and a reflector 43.

As one example, the PCB substrate 31 is electrically connected to supply power from the power supply unit 50 and generates visible light by controlling a current flow with respect to the LED 32. The LED 32 is electrically connected to the PCB substrate 31 to generate visible light with a 405 nm wavelength.

In particular, referring to transmittance performance for each wavelength in FIG. 3, there is an example of solving a problem of directivity and transmittance of the existing light which are caused by UVC light with a wavelength ranging from 100 nm to 280 nm not having light transmittance because the 405 nm wavelength of the visible light has light transmittance.

As one example, since the light guiding plate 41 is made of a light guiding film and has a predetermined width and a predetermined length, the light guiding plate 41 connects a traveling path of the visible light coming from one end thereof facing the LED 32 to the other half, and a light emitting surface is formed in which the visible light diffuses to the outside while passing through the traveling path. In this case, the light guiding film is manufactured through a roll stamping process using an extruded original sheet.

In addition, the optical ink 42 is applied or coated on the light emitting surface formed on one surface of the light guiding plate 41 to increase a light diffusion effect of the visible light, and the reflector 43 is overlaid or attached to the other surface of the light guiding plate 41 (that is, a surface to which the optical ink 42 is not coated) so that the visible light may be completely directed only toward the light emitting surface. In this case, an aluminum material may be applied to the reflector 43.

Figure 4:
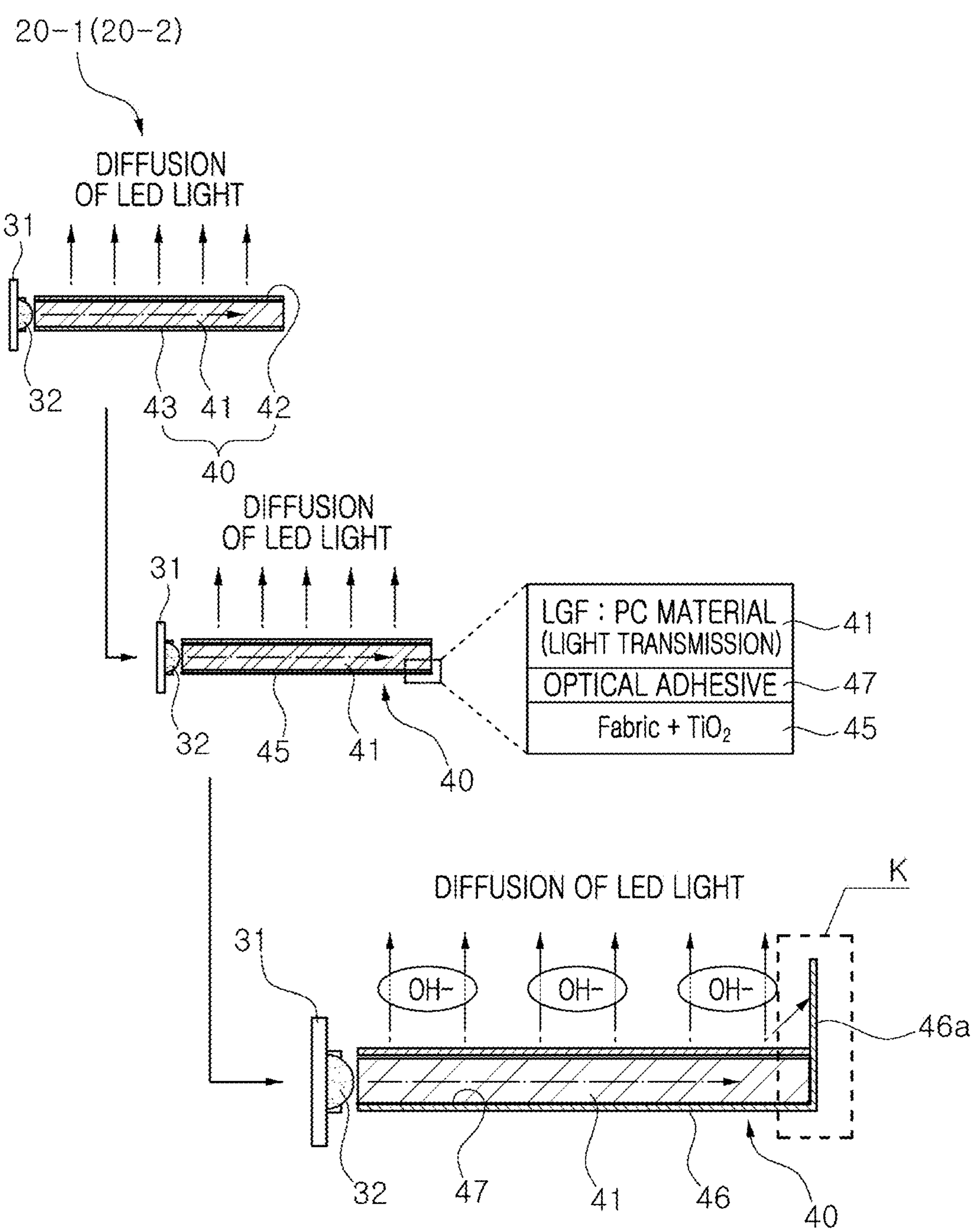
FIG. 4 is a diagram illustrating an example in which a reflector constituting a light diffusion unit of a sterilization light generator is transformed into a photocatalytic reflector or a photocatalytic extended reflector.

Meanwhile, FIGS. 4 and 5 show an example in which a photocatalyst reflector 45 or a photocatalytic extended reflector 46, in which the reflector 43 is modified, is installed the light diffusion unit 40.

Referring to FIG. 4, the light diffusion unit 40 includes the light guiding plate 41, the optical ink 42, and the reflector 43 as basic components and may include the light guiding plate 41, the optical ink 42, the photocatalyst reflector 45, and an optical adhesive 47 or may include the light guiding plate 41, the optical ink 42, the photocatalytic extended reflector 46, and the optical adhesive 47.

For example, the photocatalyst reflector 45 is formed to have the same length as the light guiding plate 41, and like the reflector 43, the photocatalyst reflector 4 is attached on the other surface of the light guiding plate 41 (i.e., the surface on which the optical ink 42 is not coated) using the optical adhesive 47.

In particular, the photocatalyst reflector 45 is manufactured by coating a fabric with a photocatalyst (titanium dioxide ($TiO_2$)), thereby inducing light diffused reflection by the fabric and improving reflectance by the photocatalyst ($TiO_2$) coating to allows the visible light to be completely transmitted only to the light emitting surface.

On the other hand, the photocatalytic extended reflector 46 forms a side section of the light guiding plate with a reflector side wall 46*a*, which further extends, in a length section of the light guiding plate having the same length as the light guiding plate 41, and like the reflector 43, the length section of the light guiding plate is attached on the other surface of the light guiding plate 41 (i.e., the surface on which the optical ink 42 is not coated) using the optical adhesive 47, and the side section of the light guiding plate is attached at an end of the light guiding plate 41 using the optical adhesive 47 to be erected vertically so that the reflector side wall 46*a* covers an LED light diffusion space at a predetermined height and the covered space is formed as a sterilizing material generation space K.

In particular, the photocatalytic extended reflector 46 is manufactured by coating a fabric with a photocatalyst (titanium dioxide ($TiO_2$)).

Therefore, the photocatalytic extended reflector 46 directs the visible light toward the light emitting surface through induction of diffused light reflection by the fabric and improvement of reflectance by the photocatalyst ($TiO_2$) in the length section of the light guiding plate and, simultaneously, the reflector side wall 46*a* generates sterilizing materials (e.g., OH and $O_2^-$) due to a reaction between some of the visible light emitted toward the light emitting surface and the photocatalyst ($TiO_2$).

As in the sterilization effect principle of FIG. 5, since the photocatalyst ($TiO_2$) coating on the reflector side wall 46*a* reacts with the visible light or UV light, the photocatalyst ($TiO_2$) collides with some of the visible light, which is generated by the LED 32 of the visible light-LED unit 30 and is emitted from the light guiding plate 41 toward the optical ink 42, to generate OH and $O_2^-$ as sterilizing materials through a chemical reaction, and the sterilizing materials (e.g., OH and $O_2^-$) are diffusely reflected in an inner space of the arm rest tray 7 in which the belongings 300 such as a mobile phone or a smartphone to be sterilized are placed (see FIG. 9) so that a simultaneous front/rear surface sterilization effect for the belongings 300 can be achieved.

Meanwhile, FIGS. 6 to 9 show detailed configurations of the power supply unit 50 and the tolerance absorber 60.

Figure 6:
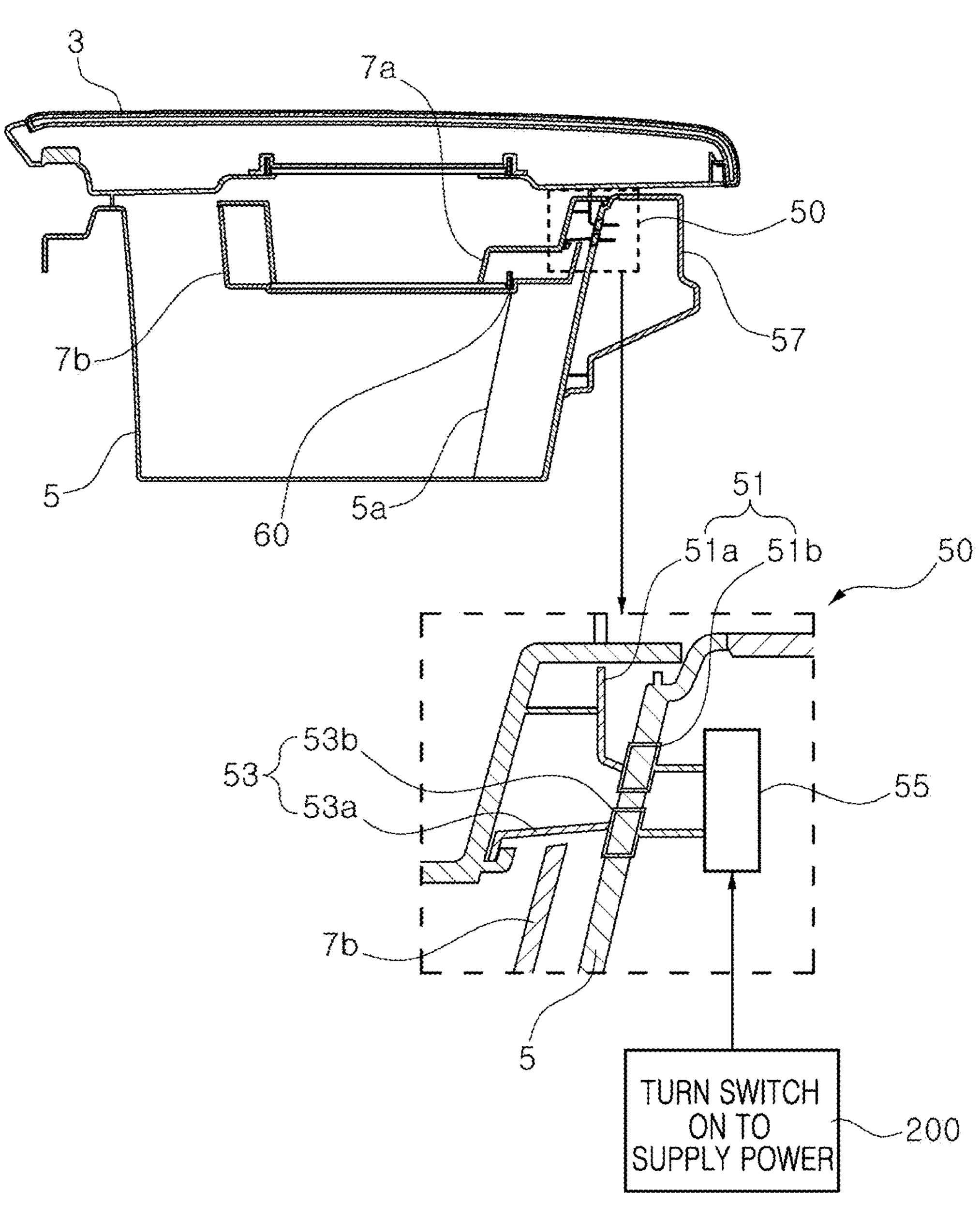
FIG. 6 is a configurational diagram illustrating an example of a power connector for supplying power to the sterilization module.

Referring to FIG. 6, the power supply unit 50 includes a first power supply 51, a second power supply 53, a power connector 55, and a protective cover 57.

As one example, the first power supply 51 is coupled to a wall surface of the console storage 5, and a power line 51*a* connected to an electrode 51*b* connected to the power connector 55 is connected to the PCB substrate 31 of the first sterilization light generator 20-1 provided in the arm rest 3 so that power of the battery 200 is conducted, and the second power supply 53 is coupled to the wall surface of the console storage 5, and a power line 53*a* connected from an electrode 53*b* connected to the power connector 55 is connected to the PCB substrate 31 of the second sterilization light generator 20-2 provided in the console storage 5 so that power of the battery 200 is conducted.

As one example, the power connector 55 is connected to the electrodes 51*b* and 53*b* and connects to a power cable connected to the battery 200. In addition, the protective cover 57 forms a cable inlet to allow the power cable to be plugged into the power connector 55 and is coupled in an attachment/detachment structure from the outside of the console storage 5 to protect the components of the power supply unit 50.

Figure 7:
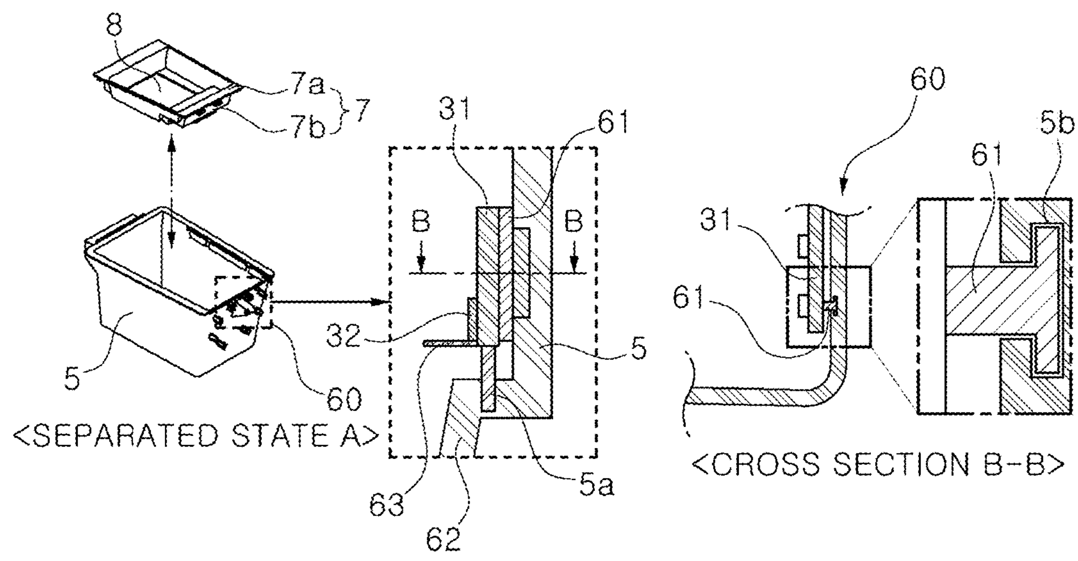
FIG. 7 is a configurational diagram illustrating an example of a tolerance absorber installed at a console storage.

Referring to separated state A of FIG. 7, the tolerance absorber 60 absorbs a distribution of a mounting position of the arm rest tray 7 with respect to the storage inner wall 5*a* of the console storage 5 in the console inner space so that the light guiding plate 41 (i.e., the second light guiding plate 41 of the second sterilization light generator 20-2) located on the bottom of the upper arm rest tray 7*a* exactly faces the second LED 32 located on the wall surface of the console storage 5 (i.e., the second LED 32 of the second sterilization light generator 20-2) to allow the visible light to directly enter the light guiding plate 41.

To this end, the tolerance absorber 60 is provided using the storage inner wall 5*a* of the console storage 5 and includes a guider 61, a spring 62, and a light guiding plate support panel 63.

As one example, the guider 61 is coupled to an inner wall of the console storage 5 to be coupled to a rear surface of the PCB substrate 31, thereby restricting positions of the PCB substrate 31 and the LED 32 and, particularly, as shown in a cross section B-B, the guider 61 is formed in a "T" cross section structure to be inserted into and constrained in a vertical slot 5*b* having a "T" cross section which is dug in a direction perpendicular to the inner surface of console storage 5. In this case, a vertical height (i.e., a vertical length) of the vertical slot 5*b* is set to allow the spring 62 to be deformed to a maximum compressed length by being pressed from an initial stretch length.

In particular, since the guider 61 is provided as two or more guiders at intervals according to a length of the PCB substrate 31, up/down movements of the PCB substrate 31 are stably maintained.

Therefore, the guider 61 moves up and down in the inner space of the console storage 5 along the vertical slot 5*b* due to a force applied from the arm rest tray 7.

As one example, the spring 62 is vertically erected in a bent portion of the storage inner wall 5*a* and is maximally stretched in an initial state in which no external force is applied to support a lower portion of the PCB substrate 31. In this case, a spring force in the stretched state of the spring 62 is set to a size that is not compressed by weights of the PCB substrate 31, the LED 32, and the guider 61.

As one example, the light guiding plate support panel 63 protrudes horizontally from the lower portion of the PCB substrate 31 to a side surface thereof and corresponds to the length of the PCB substrate 31 or a length of the light guiding plate 41. In this case, a protruding width (or a protruding length) of the light guiding plate support panel 63 is set so as not to contact a lower portion of the upper arm rest tray 7*a* in a state in which the arm rest tray 7 is coupled.

Figure 8:
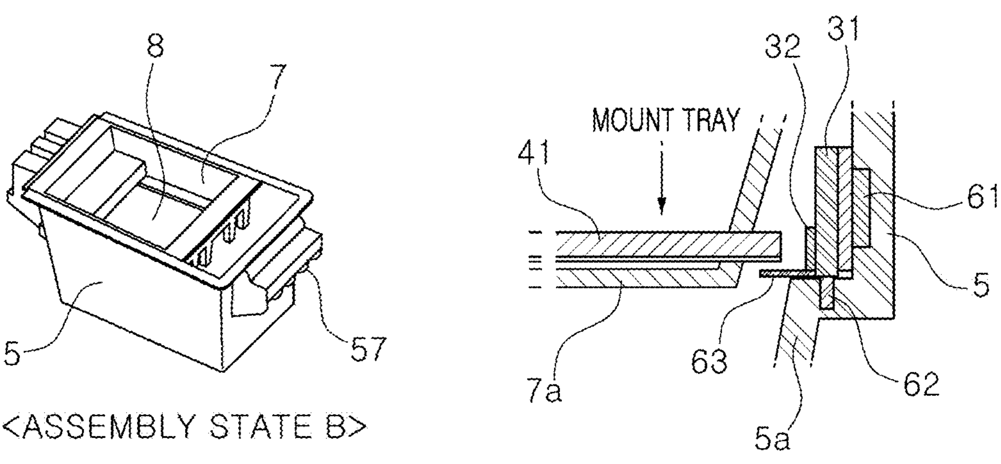
FIG. 8 is a diagram illustrating an example of a state in which an arm rest tray is seated on the tolerance absorber of the console storage.

Referring to assembly state B of FIG. 8, the arm rest tray 7 is inserted into the inner space of the console storage 5 in a state in which the light guiding plate 41 comes out of a light guiding plate groove passing through the tray inner wall forming the bottom of the upper arm rest tray 7*a*, thereby operating the tolerance absorber 60.

As one example, in a state in which the light guiding plate support panel 63 is in contact with the end of the light guiding plate 41, when the tolerance absorber 60 is moved down by receiving a downward force caused by the light guiding plate 41 that presses down, the guider 61 is moved down along the vertical slot 5*b* to support a movement of the PCB substrate 31 moved down together with the light guiding plate support panel 63, and the spring 62 is pressed to the lower portion of the PCB substrate 31 to be deformed to a maximum compressed state.

In particular, when the arm rest tray 7 is removed, the spring 62 returns to the stretched state from the compressed state with an elastic restoring force, and the elastic restoring force is set to be smaller than a force applied by a weight of the arm rest tray 7.

In this way, the tolerance absorber 60 absorbs a distribution of a mounting position of the light guiding plate to allow the light guiding plate 41 to always face the LED 32, thereby acting such that sterilization performance of visible light can always be maintained.

Figure 9:
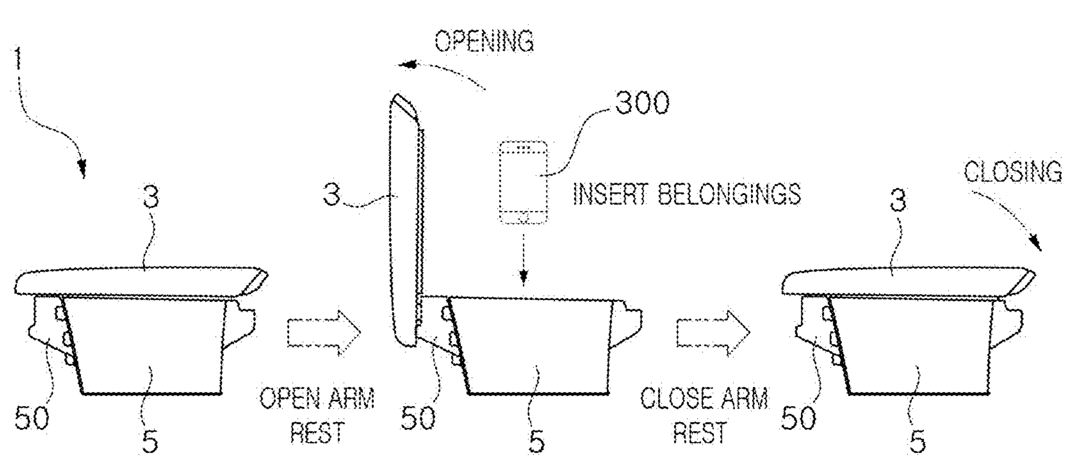
FIG. 9 is a diagram illustrating an example of a use state of the bidirectional sterilization type console arm rest device.
Figure 9:
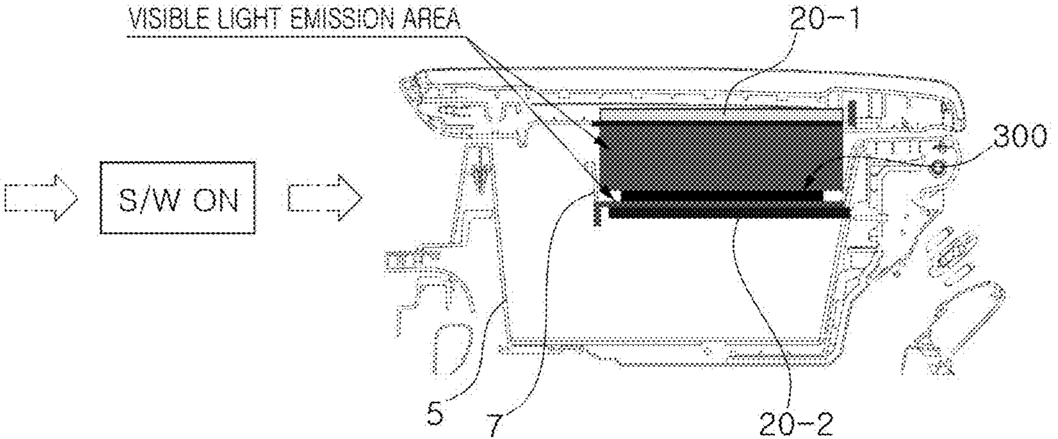

Meanwhile, FIG. 9 shows a state of the use of the bidirectional sterilization type console arm rest device 1. In this case, a description will be made in an assembly state in which the arm rest tray 7 is mounted in the inner space of the console storage 5 in a state of being provided with the light guiding plate 41 (see FIG. 6).

As shown in the drawing, in a state in which the arm rest 3 is closed in a hinge structure to cover the console storage 5, the arm rest 3 is moved up and opened, the belongings 300 are seated in the tray opening 8 of the upper arm rest tray 7*a* (see FIG. 5) and then the arm rest 3 is moved down and closed. In this case, the belongings 300 are mobile devices including mobile phones and smart phones.

In some implementations, the armrest 3 can be used to securely cover the console storage 5 when closed.

Subsequently, when the switch 9 provided at the arm rest 3 is pressed to electrically connect the battery 200 and the power supply unit 50 (see FIG. 4), power of the battery 200 is supplied to the first sterilization light generator 20-1 provided at the arm rest 3 and the second sterilization light generator 20-2 provided at the upper arm rest tray 7*a*.

Then, the first sterilization light generator 20-1 emits downward visible light from the light guiding plate 41 (i.e., the first light guiding plate), which diffuses the visible light of the LED 32 (i.e., the first LED), to front surfaces of the belongings 300, and the second sterilization light generator 20-2 emits upward visible light from the light guiding plate 41 (i.e., the second light guiding plate), which diffuses the visible light of the LED 32 (i.e., the second LED), to rear surfaces of the belongings 300.

Therefore, the sterilization action on the belongings 300 is performed in a visible light emission area by the downward visible light and the upward visible light, and thus germs on the belongings 300 are sterilized simultaneously on the front and rear surfaces of the belongings 300 so that enhancement of a health care function is implemented.

As described above, the bidirectional sterilization type console arm rest device 1 installed the vehicle 100 can include the first sterilization light generator 20-1 generating visible light from the arm rest 3, which is emitted downward to the front surfaces of the belongings 300 placed on the arm rest tray 7 assembled with the console storage 5, and the second sterilization light generator 20-2 generating visible light from the interior space of console storage 5, with which the arm rest tray 7 is assembled, emitted upward to the rear surfaces of belongings 300.

Therefore, the bidirectional sterilization type console arm rest device 1 is operated in the vehicle 100 so that sterilization by the visible light with a 405 nm wavelength solves the problem of harmfulness to the human body and the problem of light directivity and transmittance, maximizes the sterilization effect by light diffusion of the light guiding film, and reduces a production cost and, particularly, due to the separation structure of the light source and the light guiding film, when the arm rest tray is separated, the light guiding film also comes out of the belongings storage space so that usability of the tray as well as utilization of the storage space are increased.

In accordance with a bidirectional sterilization type console arm rest device installed a vehicle according to the present disclosure, due to sterilization by visible light with a 405 nm wavelength, the problem of harmfulness to the human body and the problem of light directivity and transmittance can be solved.

In addition, in accordance with the bidirectional sterilization type console arm rest device, by increasing the sterilization effect by light diffusion of the light guiding film of two light sources emitting the visible light in two directions of a mobile device, it is possible to enhance a health care function and increase marketability by removing germs spread by human hands.

In addition, in accordance with the bidirectional sterilization type console arm rest device, by employing a separation structure of the light source and the light guiding film, when an arm rest tray is separated, the light guiding film also comes out of a belongings storage space so that usability of the tray as well as utilization of the storage space can be increased.

What is claimed is:

1. A console arm rest device, comprising:

a first sterilization light generator configured to emit first visible light in a first direction toward first surfaces of a plurality of items disposed at an arm rest, the arm rest being movably coupled to a console storage accommodating an arm rest tray that is configured to receive the plurality of items in a console inner space; and a second sterilization light generator configured to emit second visible light in a second direction to second surfaces of the plurality of items in the console inner space, wherein each of the first sterilization light generator and the second sterilization light generator includes (i) a light-emitting diode (LED) mounted on a printed circuit board (PCB) substrate and configured to generate visible light and (ii) a light guiding plate configured to guide emission of the visible light by defining a traveling path of the visible light.

2. The console arm rest device of claim 1, wherein the LED and the light guiding plate are positioned separately, facing each other.

3. The console arm rest device of claim 1, wherein a wavelength of each of the first visible light and the second visible light is 405 nm.

4. The console arm rest device of claim 1, wherein the light guiding plate includes a light guiding film configured to diffuse the visible light.

5. The console arm rest device of claim 4, wherein the light guiding plate is configured to diffuse the visible light using a light emitting surface coated with optical ink.

6. The console arm rest device of claim 5, wherein the light guiding plate provides a reflector configured to reflect the visible light on a surface opposite to the light emitting surface.

7. The console arm rest device of claim 6, wherein:

the light guiding plate provides a photocatalyst reflector that is coupled to the surface opposite to the light emitting surface by an optical adhesive and that is made of (i) a fabric configured to induce diffused reflection of the visible light and (ii) a photocatalyst configured to increase reflectance, and the photocatalyst reflector defines, as a same length as the light guiding plate, a length section of the light guiding plate at which the light diffused reflection induction and the reflectance increase are performed.

8. The console arm rest device of claim 7, wherein:

the light guiding plate provides a photocatalytic extended reflector that is coupled to the surface opposite to the light emitting surface by an optical adhesive and that is made of (i) a fabric configured to induce diffused reflection of the visible light and (ii) a photocatalyst configured to increase reflectance, and the photocatalytic extended reflector provides a reflector side wall that extends from the length section of light guiding plate and disposed at a first end portion of the light guiding plate.

9. The console arm rest device of claim 8, wherein:

the photocatalytic extended reflector is configured to induce the light diffused reflection and increase the reflectance in the length section of the light guiding plate, and the reflector side wall is configured to generate a sterilizing material through a chemical reaction between the visible light emitted from the light emitting surface and a photocatalyst ($TiO_2$).

10. The console arm rest device of claim 1, wherein: the console storage is configured to receive a power supply configured to supply power from a battery to the PCB substrate and the LED.

11. The console arm rest device of claim 10, wherein the power supply is configured to supply the power of the battery through a switch provided at the arm rest.

12. The console arm rest device of claim 10, wherein the power supply includes:

a first power supply connected to the first sterilization light generator, a second power supply connected to the second sterilization light generator, a power connector connecting power cables to the first power supply and the second power supply, and a protective cover coupled to the console storage and covering the power connector.

13. The console arm rest device of claim 1, wherein:

the console storage is configured to receive a tolerance absorber in a bent portion of a storage inner wall, and the tolerance absorber is configured to absorb a distribution of a mounting position of the arm rest tray with respect to the storage inner wall in the console inner space.

14. The console arm rest device of claim 13, wherein the tolerance absorber includes:

a guider coupled to an inner wall surface of the console storage and configured to guide downward movement of the PCB substrate, a spring coupled to the bent portion of the storage inner wall and supporting a lower portion of the PCB substrate, and a light guiding plate support panel configured to, based on the arm rest tray being located in the bent portion of the storage inner wall, move the PCB substrate downward by receiving a force applied downward by the light guiding plate.

15. The console arm rest device of claim 14, wherein the guider has a "T" cross section structure.

16. The console arm rest device of claim 14, wherein the spring is configured to be compressed by the downward movement of the PCB substrate.

17. The console arm rest device of claim 14, wherein the light guiding plate support panel protrudes horizontally from a side surface of the PCB substrate.

18. The console arm rest device of claim 1, wherein:

an arm rest cover is provided at a lower portion of the arm rest, and the first sterilization light generator is disposed at the arm rest cover.

19. The console arm rest device of claim 1, wherein:

the arm rest tray defines a tray opening, and the tray opening defines a rim on which the plurality of items are received.

20. A vehicle, comprising:

a console arm rest including (i) an arm rest configured to open within a console storage defining a console inner space and (ii) an arm rest tray configured to receive a plurality of items and detachably coupled to the console inner space; and a sterilization module including (i) a first sterilization light generator disposed at the arm rest and configured to emit first visible light in a first direction toward first surfaces of the plurality of items and (ii) a second sterilization light generator disposed at the console inner space and configured to emit second visible light in a second direction toward second surfaces of the plurality of items.

21. The vehicle of claim 20, wherein:

the sterilization module includes a power supply disposed at the console storage, and the power supply is configured to supply power of a battery to the first sterilization light generator and the second sterilization light generator through a switch disposed at the arm rest.

22. The vehicle of claim 20, wherein:

the sterilization module includes a tolerance absorber coupled to a storage inner wall extending toward the console inner space of the console storage, and the tolerance absorber is configured to absorb a distribution of a mounting position of the arm rest tray with respect to the storage inner wall in the console inner space.

* * * * *